US00PP31437P2

(12) United States Plant Patent
Avent

(10) Patent No.: US PP31,437 P2
(45) Date of Patent: Feb. 11, 2020

(54) ***YUCCA* PLANT NAMED 'SILVER ANNIVERSARY'**

(50) Latin Name: ***Yucca filamentosa* x *Yucca pallida***
Varietal Denomination: Silver Anniversary

(71) Applicant: Tony Avent, Raleigh, NC (US)

(72) Inventor: Tony Avent, Raleigh, NC (US)

( * ) Notice: Subject to any disclaimer, the term of this patent is extended or adjusted under 35 U.S.C. 154(b) by 0 days.

(21) Appl. No.: 16/350,695

(22) Filed: Dec. 19, 2018

(51) Int. Cl.
*A01H 5/02* (2018.01)
*A01H 6/12* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Karen M Redden
(74) *Attorney, Agent, or Firm* — Barbara Campbell; Cochran Freund & Young LLC

(57) ABSTRACT

A new cultivar of *Yucca* plant named 'Silver Anniversary' that is characterized by compact habit, moderate plant vigor, production of multiple offsets, powder-blue colored foliage which is hardy in USDA Zone 5b, and a tall inflorescence consisting of burgundy stems and cream-white flowers, is disclosed.

2 Drawing Sheets

Genus and species: *Yucca filamentosa* x *Yucca pallida*.
Variety denomination: 'Silver Anniversary'.

BACKGROUND OF THE NEW PLANT

The present invention relates to a new and distinct variety of *Yucca*, commonly known as soapwort, which is grown for use as an ornamental plant for planted containers or for planting in the landscape. 'Silver Anniversary' is known botanically as *Yucca filamentosa* x *Yucca pallida* and will be referred to hereinafter by the cultivar name 'Silver Anniversary'.

'Silver Anniversary' arose from a *Yucca* breeding program commenced by the inventor in a nursery in Raleigh, N.C. in 2013. The goals of the breeding program were to develop novel varieties which grow and multiply rapidly while maintaining a compact habit, and developing varieties with striking foliage color and cold-hardiness in zone 7b. 'Silver Anniversary' was selected from a population of diverse seedlings which were raised from seed arising from the open-pollination of two species of *Yucca*: the female parent, an unknown *Yucca filamentosa*, commonly known as Adam's needle, and the male parent, an unknown *Yucca pallida*, commonly known as pale *Yucca*. A single seedling, designated 'Silver Anniversary', exhibited a combination of greatly increased vigor, presumably arising from the more vigorous species *Yucca filamentosa*, with the attractive powder-blue colored foliage of *Yucca pallida*.

'Silver Anniversary' was first propagated in 2016 at a nursery in Raleigh, N.C., using the method of division of underground stems. The inventor has observed that all asexually reproduced plants of 'Silver Anniversary' have remained stable and have reproduced true to type in successive generations of asexual reproduction via division of underground stems.

SUMMARY

The following traits have been repeatedly observed and represent the distinguishing characteristics of the new *Yucca* variety named 'Silver Anniversary'. In combination, these traits set 'Silver Anniversary' apart from all other varieties of *Yucca* known to the inventor. 'Silver Anniversary' has not been tested under all possible conditions and phenotypic differences may be observed with variations in environmental, climatic and cultural conditions, however, without any variance in genotype:

1. In its first year of growth, 'Silver Anniversary' establishes a single stemless tight rosette of foliage.
2. In successive years of growth, 'Silver Anniversary' produces multiple offsets of rosetted foliage.
3. The emerging and juvenile foliage of 'Silver Anniversary' exhibits gentle recurving which straightens as the plant and foliage matures.
4. The leaves of 'Silver Anniversary' are powder-blue in color.
5. After four months in the ground (after planting a well-rooted division), 'Silver Anniversary' is 30 cm in height and width.
6. After twelve months in the ground, 'Silver Anniversary' achieves 120 cm in height and 70 cm in width (excluding the height of the inflorescence).
7. 'Silver Anniversary' produces its first inflorescences after one year of growth.
8. The inflorescence of a mature plant of 'Silver Anniversary' will extend 75 cm to 1 m above the foliage canopy.
9. The stems of the inflorescence of 'Silver Anniversary' are burgundy in color.
10. The flowers of the inflorescence of 'Silver Anniversary' are bell-shaped and cream-white in color.
11. 'Silver Anniversary' is hardy in USDA Zones 5b to 10b.

DESCRIPTION OF THE PHOTOGRAPHS

The accompanying color photographs illustrate the overall appearance of the new *Yucca* variety named 'Silver Anniversary' showing color as true as it is reasonably possible to obtain in color reproductions of this type. Both drawings were made from photographs of an established in-ground plant growing at a nursery in Raleigh, N.C.

Figure 1:
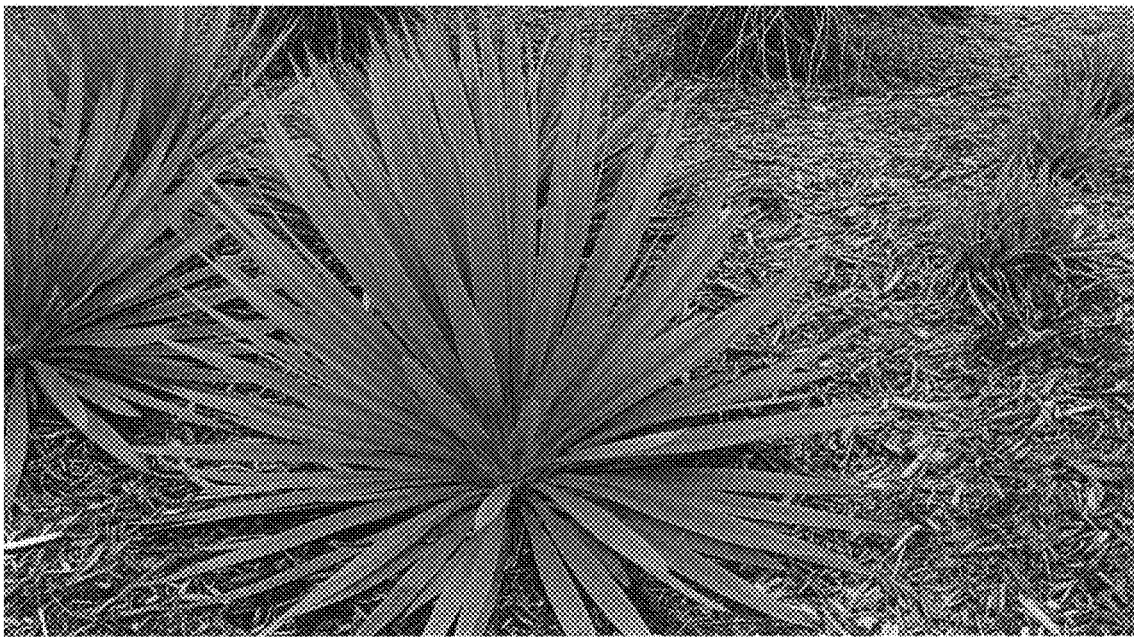
FIG. 1 depicts a one-year-old plant of 'Silver Anniversary'. No flowers have been produced in the first growing season.
Figure 2:
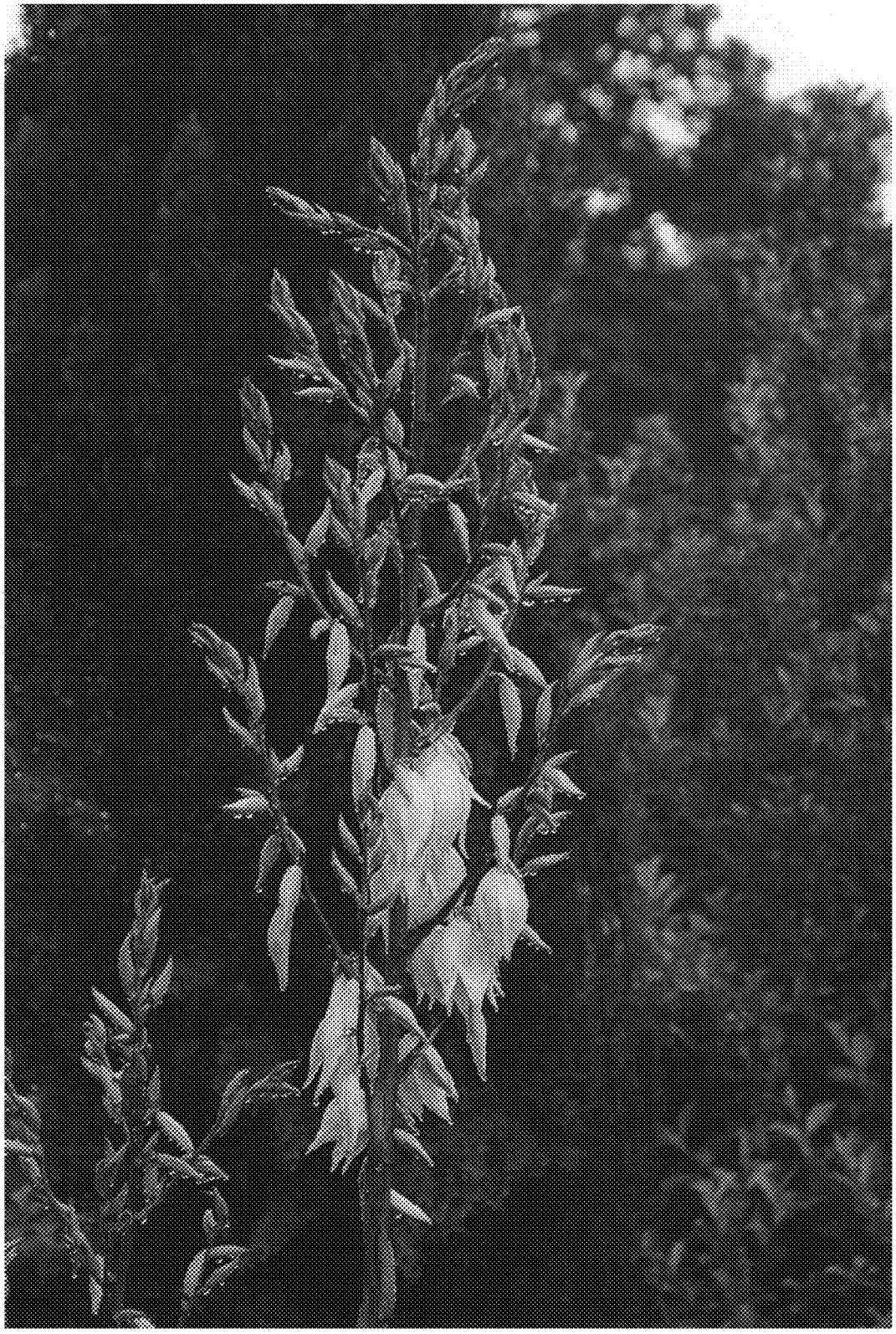
FIG. 2 depicts a close-up view of the inflorescence of 'Silver Anniversary' which was observed on a three-year-old in-ground plant.

Photographs were made using conventional techniques and although flower and foliage color may appear different from actual color due to light reflectance, they are as accurate as possible by conventional photography.

DESCRIPTION OF THE NEW VARIETY

The following is a detailed botanical description of the new *Yucca* cultivar named 'Silver Anniversary'. Data was compiled from plants grown outdoors in Raleigh, N.C. The observed plants were 3-years-old. All color determinations are in accordance with the 2007 edition of The Royal Horticultural Society Colour Chart except where general color terms of ordinary dictionary significance are used.

Botanical and plant description:

*Family.*—Asparagaceae.

*Genus.*—*Yucca.*

*Species.*—*filamentosa* x *pallida.*

*Common name.*—Soapwort.

*Use.*—Ornamental plant for use in planted containers or in the landscape.

*Parentage.*—'Silver Anniversary' arose as a selected seedling from a population of plants raised from seed resulting from the open-pollination of plants of the two species *Yucca filamentosa* and *Yucca pallida.*

*Habit.*—Compact, dome-shaped foliage canopy.

*Vigor.*—Moderate overall plant growth (plant size); vigorous production of offsets.

*Plant dimensions* (*in-ground, excluding inflorescence*).—After four months, 30 cm in height and width. After twelve months, 120 cm in height, 70 cm in width. After three years, 1.5 m in height, 1 m in width.

*Plant hardiness.*—5b to 10b.

*Propagation.*—Division of underground stem or root cuttings. Division of basal shoots in tissue culture.

*Root system.*—Fine and fibrous.

*Time to develop roots.*—2 months to full rooting in a quart container.

*Crop time.*—2 months after planting a rooted division in a quart container; 6 months after planting a quart container into a 1-gallon container.

*Disease susceptibility and resistance.*—Susceptible to *Yucca* Plant Bug, *Halticotoma valida.*

*Special growing considerations.*—'Silver Anniversary' is adaptable but prefers well-drained soil and a full-sun to part-sun aspect.

*Drought/heat tolerance.*—This variety withstands the hot and humid conditions of Raleigh, N.C. (zone 7b), and is tolerant of drought once established.

*Stem.*—None visible above ground; 'Silver Anniversary' is acaulescent.

Foliage:

*Quantity of leaves.*—Very numerous; exceeds 250 on a 3-year-old plant.

*Leaf shape.*—Oblanceolate.

*Leaf division.*—Simple.

*Leaf arrangement.*—Spirally arranged.

*Leaf apex.*—Acuminate with apical spine.

*Shape of apical spine.*—Keel-shaped.

*Color of apical spine.*—RHS 167A.

*Length of apical spine.*—4.0 mm to 14.0 mm.

*Leaf base.*—Truncate.

*Venation pattern.*—Parallel; veins barely visible on either surface.

*Leaf margins.*—Entire; outermost edges appear white or translucent.

*Leaf attachment.*—Sheathing.

*Leaf surfaces* (*both upper and lower*).—Scabrous.

*Leaf pubescence.*—None.

*Leaf width* (*widest point, approximately halfway between base and apex*).—39.0 mm.

*Leaf length.*—Up to 69.0 cm.

*Leaf color* (*both surfaces*).—Close color match not found: between RHS 188D and RHS 122D.

Inflorescence:

*Bloom period.*—May to June.

*Inflorescence diameter.*—30.0 cm.

*Form.*—Panicle.

*Flowers per panicle.*—350 to 450.

*Inflorescence height, from ground level.*—1.7 m to 2.0 m; 60.0 cm to 70.0 cm for inflorescence only.

*Flower diameter.*—1.2 cm to 1.6 cm.

*Stem.*—Scape, borne above foliage and extending to 111 cm to 134 cm height above foliage.

*Stem length.*—18 cm to 22 cm.

*Stem diameter.*—3 cm to 4 cm.

*Stem color.*—Emerges light green, becomes (or ages to) RHS 143C and RHS 144A.

Flowers:

*Arrangement.*—Alternate and composed of 6 tepals.

*Type.*—Campanulate.

*Tepal height or length.*—4.5 cm to 5.5 cm.

*Tepal width.*—1.6 cm to 2 cm.

*Tepal shape.*—Ovate.

*Tepal apex.*—Acuminate.

*Tepal color.*—Creamy white (RHS 155A).

*Tepal texture.*—Leathery.

*Petal dimensions, color, texture if different.*—No difference, all tepals.

*Fragrance.*—Present, musty.

*Lastingness of individual flower.*—1 to 4 days.

*Lastingness of inflorescence.*—20 to 30 days, with stalk persisting until next season.

*Pedicel.*—Absent; flowers are sessile.

Reproductive organs:

*Stamens.*—6 in number; 1.6 mm to 1.8 mm in length; color: white.

*Anthers.*—Small, globular; color: brown/yellow.

*Pistils.*—3.

*Stigma.*—White.

*Pollen quantity.*—Slight; color: Creamy white.

*Fruit or capsules.*—Dry dehiscent capsule.

*Seed.*—Papery, black.

COMPARISON TO PARENTAL LINES

'Silver Anniversary' may be compared with its parents as follows. Whereas the female parent *Yucca filamentosa* has green foliage, the foliage of 'Silver Anniversary' is powder blue in color. Whereas the male parent *Yucca pallida* and 'Silver Anniversary' both bear powder blue foliage, plants of 'Silver Anniversary' exhibit greatly increased vigor.

The variety which the inventor considers to most closely resemble 'Silver Anniversary' is 'TUSZYUC001' (U.S. Plant Pat. No. 29,025) and is distinguished from the commercial comparison in Table 1.

TABLE 1

| Comparison with Similar Variety | | |
|---|---|---|
| Trait | 'Silver Anniversary' | 'TUSZYUC001' |
| Plant height and width (maturity) | 120 cm and 70.0 cm | 35 cm and 35 cm |

I claim:

1. A new and distinct variety of *Yucca* plant named 'Silver Anniversary' as illustrated and described herein.

* * * * *